(12) United States Patent
Lee et al.

(10) Patent No.: US 12,157,012 B2
(45) Date of Patent: Dec. 3, 2024

(54) LOW EMF INFRARED RADIANT PANEL

(71) Applicant: Sunlighten, Inc., Overland Park, KS (US)

(72) Inventors: Jui-Hsing Lee, Taichung (CN); Aaron Michael Zack, Overland Park, KS (US); Dustin Stevens, Overland Park, KS (US)

(73) Assignee: Sunlighten, Inc., Overland Park, KS (US)

( * ) Notice: Subject to any disclaimer, the term of this patent is extended or adjusted under 35 U.S.C. 154(b) by 0 days.

(21) Appl. No.: 18/255,556

(22) PCT Filed: Mar. 26, 2021

(86) PCT No.: PCT/US2021/024507
§ 371 (c)(1),
(2) Date: Jun. 1, 2023

(87) PCT Pub. No.: WO2022/139862
PCT Pub. Date: Jun. 30, 2022

(65) Prior Publication Data
US 2023/0398373 A1    Dec. 14, 2023

(30) Foreign Application Priority Data

Dec. 25, 2020   (CN) .......................... 202011568541.6

(51) Int. Cl.
*A61N 5/06*       (2006.01)
*H05B 3/10*       (2006.01)
(Continued)

(52) U.S. Cl.
CPC ............. *A61N 5/0625* (2013.01); *H05B 3/10* (2013.01); *H05B 3/20* (2013.01); *H05B 3/66* (2013.01);
(Continued)

(58) Field of Classification Search
CPC .................... A61N 5/0625; A61N 5/06; A61N 2005/0632; A61N 2005/0652; A61N 2005/066; A61N 2005/0659; H05B 3/10; H05B 3/20; H05B 3/66; H05B 3/267; H05B 1/025; H05B 2203/003; H05B 2203/037; H05B 2203/013; H05B 2203/032; Y02B 30/00
See application file for complete search history.

(56) References Cited

U.S. PATENT DOCUMENTS 5,969,369 A * 10/1999 Fogarty ...................... F41J 2/02
                                                    250/504 R
6,561,794 B1 * 5/2003 Narasimhan ............ F23D 14/16
                                                    277/645
(Continued)

FOREIGN PATENT DOCUMENTS

WO      2018065755 A1    4/2018

*Primary Examiner* — Shawntina T Fuqua
(74) *Attorney, Agent, or Firm* — AVEK IP, LLC; Kent R. Erickson

(57) ABSTRACT

An infrared radiant panel is formed by overlaid substrates having conductors thereon which are electrically activated to generate heat to cause infrared radiation of desired wavelengths. The conductors are arranged to cancel magnetic fields caused by current flow therethrough. A conductive shield further suppresses fields generated by the panel.

18 Claims, 5 Drawing Sheets

(51) Int. Cl.
*H05B 3/20* (2006.01)
*H05B 3/66* (2006.01)

(52) U.S. Cl.
CPC ............. *A61N 2005/0632* (2013.01); *A61N 2005/0652* (2013.01); *A61N 2005/066* (2013.01)

(56) References Cited

U.S. PATENT DOCUMENTS

| | | | |
|---|---|---|---|
| 7,120,353 | B2 | 10/2006 | Schaeffer et al. |
| 8,737,827 | B2 * | 5/2014 | Zack ................ H05B 3/10 392/407 |
| 10,869,367 | B2 | 12/2020 | Duncan et al. |
| 11,641,702 | B2 | 5/2023 | Duncan et al. |
| 2007/0129776 | A1 * | 6/2007 | Robins ............. A61N 5/0613 607/88 |
| 2007/0269205 | A1 * | 11/2007 | Lee ................. G03B 17/02 396/542 |
| 2011/0081135 | A1 * | 4/2011 | Felder ............. A21C 15/002 392/407 |
| 2012/0241440 | A1 * | 9/2012 | Duncan ............ H05B 6/44 219/600 |
| 2012/0307976 | A1 * | 12/2012 | Kaneko ............ G21K 1/025 378/62 |
| 2013/0319998 | A1 | 12/2013 | Benda et al. |
| 2014/0209592 | A1 * | 7/2014 | Pereira ........... B64D 15/12 219/205 |
| 2017/0189266 | A1 | 7/2017 | Johnson |
| 2020/0384288 | A1 * | 12/2020 | Daffer ............. A61N 5/0616 |

\* cited by examiner

LOW EMF INFRARED RADIANT PANEL

CROSS-REFERENCE TO RELATED APPLICATIONS

This application claims priority from Chinese Patent Application No. 2020115685416, filed Dec. 25, 2020 the disclosure of which is hereby incorporated herein in its entirety by reference.

BACKGROUND

Field of the Invention

This invention relates to radiant infrared panels for therapeutic purposes and, more particularly, to such a panel radiating infrared (IR) energy in multiple wavelength ranges which may develop low electromagnetic fields (EMF) varying at extremely low frequencies (ELF).

Background & Description of Related Art

Infrared therapy uses infrared heaters to emit infrared energy as radiant heat which is absorbed by the skin and body. There are numerous studies which indicate health benefits result from infrared radiation in areas such as stress reduction, injury healing, pain reduction, toxin elimination, heart function, immunity improvements, and the like. Infrared therapy is somewhat similar to sauna and steam bath therapies which have existed in various forms in various cultures for centuries.

Infrared energy can be radiated in various infrared wavelength ranges from infrared light emitting diodes (LED's), from infrared lamps, and from flat infrared radiant panels. Polyimide (PI) heaters are a type of radiant heater panel formed from a sheet or layer of a polyimide polymer. Polyimide heaters may be manufactured in a manner similar to printed circuit boards. A layer or substrate of polyimide is formed with a resistive conductor cladding which is etched to form a pattern of conductors that are electrically activated to generate heat. Polyimides are generally heat tolerant and may be rigid or have some degree of flexibility.

One or more infrared radiant polyimide heater panels may be supported on a wall in an existing room or within an enclosed structure, referred to as an infrared sauna, within a home, such as the types of structures disclosed in U.S. Pat. Nos. 7,458,111 or 8,676,044, the disclosures of which are incorporated herein in their entireties by reference. Such structures may be self-supporting buildings constructed outdoors. Support structures for such panels may also be provided in commercial, therapeutic, or rehabilitation settings.

An area of concern regarding radiant panels generating heat from lengths of conductors is the creation of electromagnetic fields (EMF), including extremely low frequency (ELF) fields. There are concerns that interactions of electromagnetic fields with various human tissues can cause undesirable changes or conditions in such tissues.

SUMMARY

Exemplary embodiments of the present invention provide a low EMF radiant infrared (IR) panel which includes: a nonconductive substrate having opposite substrate surfaces, a first infrared region formed on a surface of the substrate to radiate infrared energy in a first range of wavelengths, and a second infrared region formed on a surface of the substrate or another substrate to radiate infrared energy in a second range of wavelengths. Each of the infrared regions includes a first conductor formed on a first surface of the substrate in a selected pattern and a second conductor formed on a second surface of the substrate or another substrate in the selected pattern, the second conductor being positioned in close adjacent relation to the first conductor and being aligned therewith. The first and second conductors receive levels of electrical current required to generate heat to cause infrared radiation in the range of wavelengths associated with the respective infrared region. The first and second conductors are electrically activated in opposite polarities to cause cancellation of components of electromagnetic fields resulting from currents flowing in the conductors. A conductive electromagnetic shield layer is positioned in covering relation to the first and second infrared regions to suppress additional electromagnetic field components resulting from currents flowing through conductors thereof.

An embodiment of the panel includes a plurality of the substrates. Each of the conductors of an infrared region is formed in the selected pattern on a surface of a separate substrate. The substrates are positioned in adjacent overlying relation with the conductors positioned in close adjacent relation to cause cancellation of components of electromagnetic fields resulting from currents flowing in the conductors. The substrates may be joined in mutually overlaying relation, as by being fused together. The panel may include a support frame with which the panel is structurally engaged. One or more of the substrates may have material formed on surfaces thereof to facilitate attachment of the substrates to such a support frame.

In an embodiment of the panel, each of the first and second conductors extends on its respective surface in a pattern in which a substantial portion of a first segment of each conductor is in closely adjacent, parallel relation with a substantial portion of a second segment of the conductor such that currents are flowing in opposite directions in the first and second segments to thereby cause cancellation of components of electromagnetic fields generated by currents flowing in the segments.

In an embodiment of the panel, a third infrared region is formed on the panel by a plurality of infrared emitting diodes capable of radiating infrared energy in a third range of infrared wavelengths.

The infrared radiant panel may include a direct current power supply coupled to the first and second conductors which causes the levels of current to flow therein to cause infrared radiation in the ranges of wavelengths associated with the respective infrared regions.

Embodiments of the infrared radiant panel may include a thermostat thermally engaged with each of the infrared regions. The thermostats are connected to the conductors associated with the infrared region and control current flow therein to maintain a selected range of temperatures within the infrared region to thereby maintain the range of infrared wavelengths radiated by the infrared region. The panel may include a thermal emissive material formed onto a surface of a substrate of the panel to enhance infrared radiation from the panel.

Various objects and advantages of the present invention will become apparent from the following description taken in conjunction with the accompanying drawings wherein are set forth, by way of illustration and example, certain exemplary embodiments.

The drawings constitute a part of this specification, include exemplary embodiments, and illustrate various objects and features thereof.

DETAILED DESCRIPTION OF THE PREFERRED EMBODIMENTS

Figure 1:
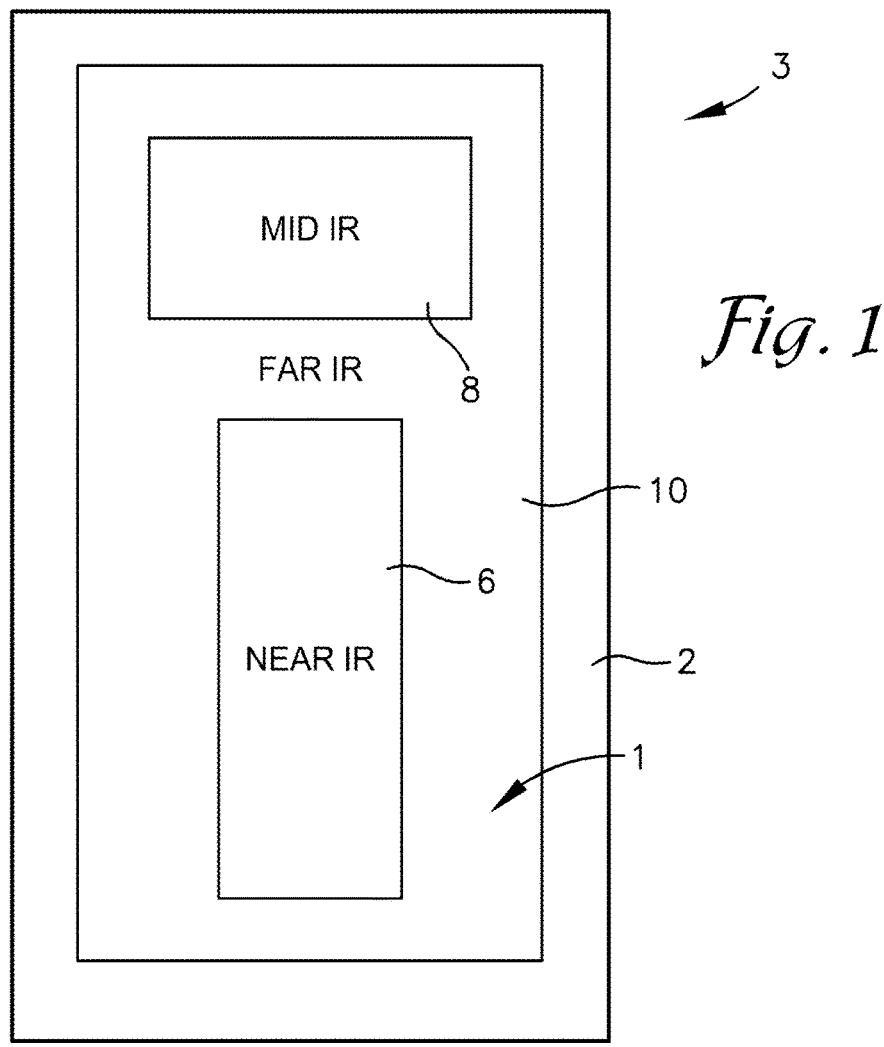
FIG. 1 is a diagrammatic elevational view illustrating an infrared radiant panel attached to a support frame depicted in accordance with an exemplary embodiment.

As required, detailed exemplary embodiments are disclosed herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to variously employ exemplary embodiments in virtually any appropriately detailed structure.

Referring to the drawings in more detail, the reference number 1 generally designates an infrared or IR radiant panel according to an exemplary embodiment. The panel 1 may be secured to a panel support frame 2 to form an infrared radiant panel structure 3. In general, the panel 1 is formed with multiple IR radiant regions 6, 8, and 10 which radiate infrared energy in multiple infrared wavelength ranges for health and therapeutic purposes.

On the illustrated panel 1, the IR radiant region 6 is designated a near IR region, the region 8 is designated a middle or mid IR region, and the region 10 is designated a far IR region. The designation of near, mid, and far infrared wavelength regions of the electromagnetic spectrum are not precisely defined in the scientific communities. For purposes herein, the near IR region will refer to IR wavelengths of about 750 to 1500 nanometers (nm); the middle or mid IR region will refer to wavelengths of about 1500 to 5000 nm, and the far IR region will refer to wavelengths of about 5000 nm to 1 millimeter (mm). The near IR range is close to and overlaps the visible range of light.

Figure 3:
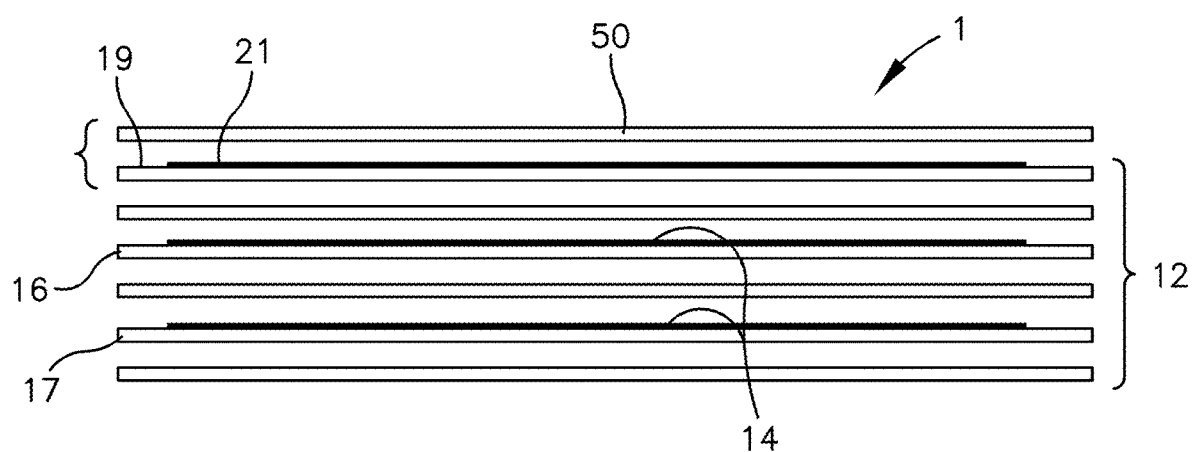
FIG. 3 is an enlarged exploded view of a plurality of substrates which are joined to form an infrared radiant panel in accordance with an exemplary embodiment.

Referring to FIG. 3, an embodiment of the IR radiant panel 1 is formed by a plurality of insulative substrates or layers 12 which have a tolerance for elevated levels of heat without substantial weakening or deforming. The substrates 12 may be formed of a material such as a polyimide or PI polymer. It is foreseen that the substrates 12 could alternatively be formed of other suitable nonconductive materials, such as polypropylene (PP), polyvinyl chloride (PVC), or the like. Some of the substrates 12 may have conductive traces or conductors 14 formed on respective surfaces thereof to generate heat to cause infrared radiation. The illustrated panel 1 has substrates 16 and 17 on which conductors 14 are formed. The substrates 12 without conductors 14 contribute to the structural strength of the panel 1 and to the desired stiffness or flexibility of the panel 1. Additionally, the substrates 12 may contribute to the thermal mass of the panel 1 which enables it to store heat, providing thermal "inertia" against undesired temperature fluctuations. One of the substrates 12 which forms a front side 19 of the panel 1 may be coated with a high emissivity material 21 which enhances the radiation of heat from the panel 1. The material 21 may, for example, be a layer of a carbon material.

The conductors 14 are electrically resistive such that the flow of electrical current therethrough generates heat in the panel 1. The conductors 14 have selected resistivity and lengths such that flow of a selected level of current therethrough generates heat of selected levels to cause radiation of infrared energy from the radiant regions 8 and 10 of the desired wavelengths. The conductors 14 may be formed on the surfaces of the substrates 12 in a manner similar to conventional printed circuit manufacturing methods. Typically, the substrates 16 and 17 intended to receive the conductors 14 are clad with the conductive material which is etched to form the conductors 14 in the desired patterns. While the near IR region 6 could also be formed using resistive conductors 14, an embodiment of the panel 1 employs an array 24 (FIG. 5) of infrared light emitting diodes or IR LED's which radiate infrared energy in the near IR region.

Figure 4:
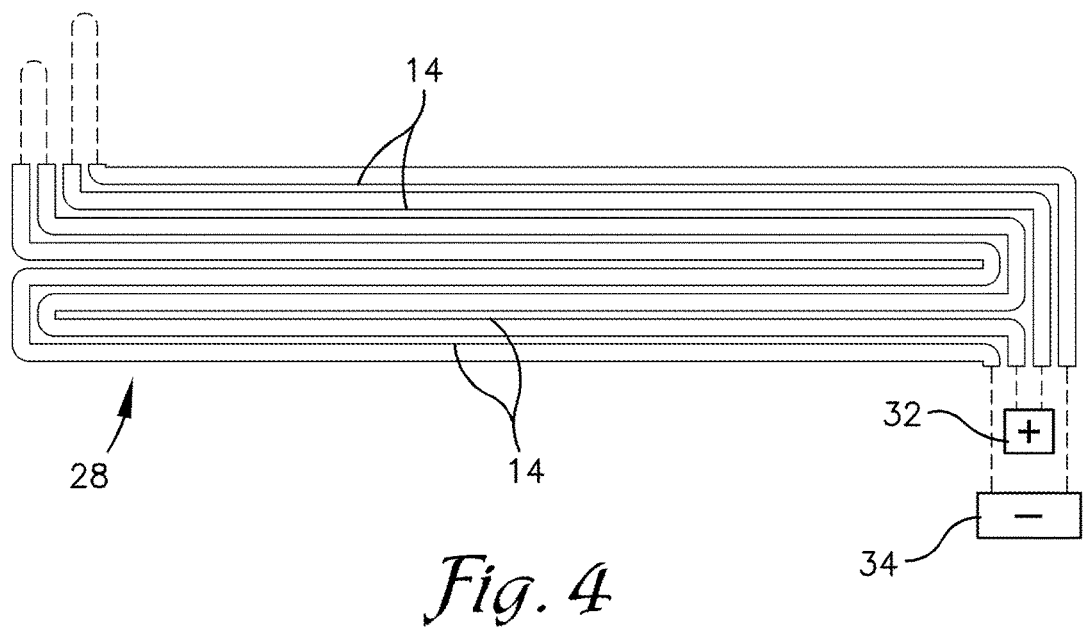
FIG. 4 is a greatly enlarged diagrammatic view of an exemplary pattern of resistive conductor traces formed on selected surfaces of substrates of an infrared radiant panel in accordance with an exemplary embodiment.

FIG. 4 illustrates a type of pattern 28 in which the conductors 14 may be arranged to form the IR regions 8 and 10. Each conductor 14 is arranged in a "bifilar" configuration in which substantial portions of the conductor extend in adjacent parallel relation out and back to a pair of electrical contact pads 32 and 34 which are connected to a power supply 37 (FIG. 2) as will be described further below. Current flowing in the adjacent portions of the same conductor 14 will be in opposite directions at any given time. Thus, an electromagnetic field generated in one portion of the conductor will be equal in magnetic field strength and opposite in magnetic polarity whereby substantial portions of the fields will be cancelled. FIG. 4 illustrates two bifilarly arranged conductors 14 which are arranged in a convoluted manner so that additional magnetic field cancellations occur between adjacent portions of the two conductors 14.

In FIG. 4, the contact pad 32 is shown with a plus sign indicating a positive polarity while the contact pad 34 is shown with a minus sign indicating negative polarity. It is foreseen that the polarities of the contact pads 32 and 34 could be reversed. Additionally, if the conductors 14 are activated by alternating current (AC), the polarity of the contact pads 32 and 34 will be periodically reversed. It is to be understood that, at all times, the contact pads 32 and 34 are at opposite electrical polarities.

Figure 2:
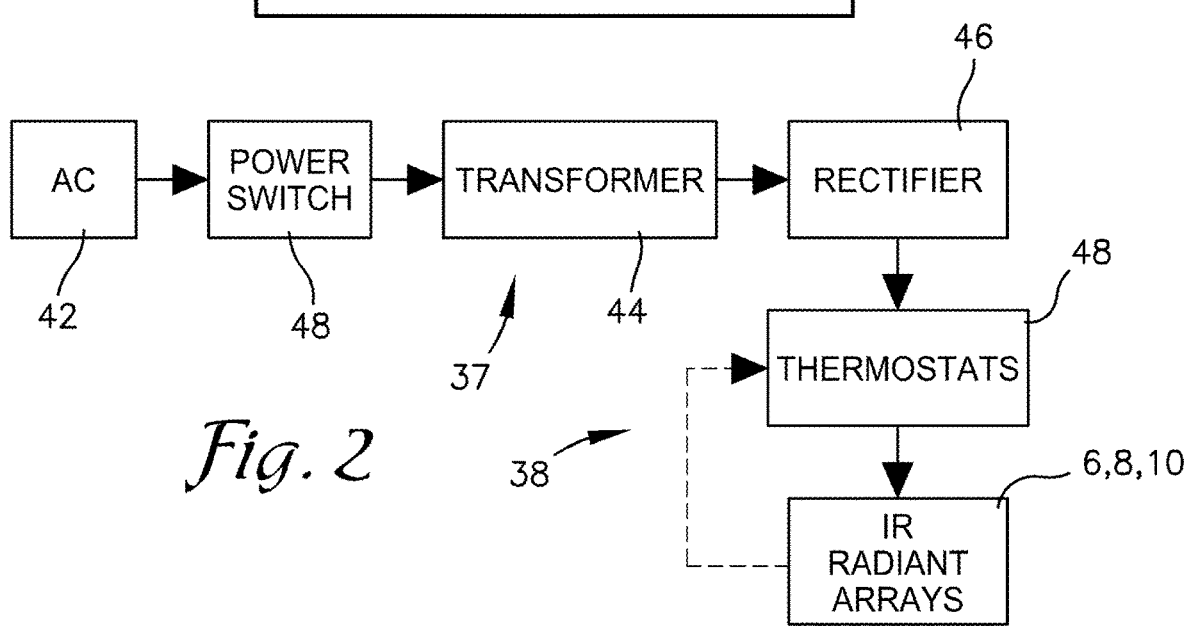
FIG. 2 is a block diagram illustrating electrical components of a power supply for an infrared radiant panel depicted in accordance with an exemplary embodiment.

FIG. 2 illustrates an exemplary power supply 37 for circuitry 38 of the panel 1, including the infrared radiant arrays 6, 8, and 10 of the panel 1. The illustrated power supply 37 includes a power switch 40 connecting an alternating current (AC) power line or AC mains 42 to a power transformer 44. The transformer 44 may be a step-down transformer to supply a lower level of voltage to the following stages of the circuitry 38. The transformer 44 also isolates the remaining stages from the power line 42. Although not shown, a fuse or circuit breaker may be incorporated between the power line 42 and the switch 40 to protect the circuitry 38. The illustrated power supply 37 is a direct current (DC) power supply and includes a rectifier 46, which may be a half-wave rectifier or a full-wave rectifier, to convert the AC power from the power line 42 to direct current. It is foreseen that a filter capacitor (not shown) could be connected to the rectifier 46 to filter ripple in the rectified direct current. It is also foreseen that alternating current could alternatively be used to power the panel circuitry 38. An exemplary embodiment of the panel 1 consumes approximately 300 watts. It is foreseen that panels 1 in exemplary embodiments could be operated at other power levels.

Each of the infrared radiant regions 6, 8, and 10 may include a respective thermostatic circuit or thermostat 48 to sense the temperature of the region and control current flow thereto to maintain a desired temperature of the region. A simple thermostat 48 enables current flow to the respective region when the sensed temperature is below a set temperature. If the temperature of the region exceeds the set temperature, the thermostat cuts off current flow thereto until the temperature drops below the set temperature. A more complex thermostatic controller circuit (not shown) varies the current flow to maintain the temperature within a close range of the set temperature.

The patterns 28 of the conductors 14 may be formed in various lengths, widths, and densities to form the IR regions 8 and 10. In general, for a given level of current, a greater density of conductors 14 per unit area generates a higher temperature in the conductors and in the substrates 12 in the vicinity of such conductors. In the illustrated panel 1, the conductors 14 are considerably denser in the mid IR region 8 than in the far IR region 10. The conductors 14 and current level therethrough of the illustrated panel 1 cause the mid IR region 8 to operate at a temperature range of about 250 to 300° F. (about 120 to 150° C.). In contrast, the conductors 14 and current level therethrough cause the far IR region 10 to operate at a temperature range of about 120 to 220° F. (about 80 to 105° C.). It is foreseen that the regions 8 and 10 could alternatively be operated at lower or higher temperatures.

Figure 5:
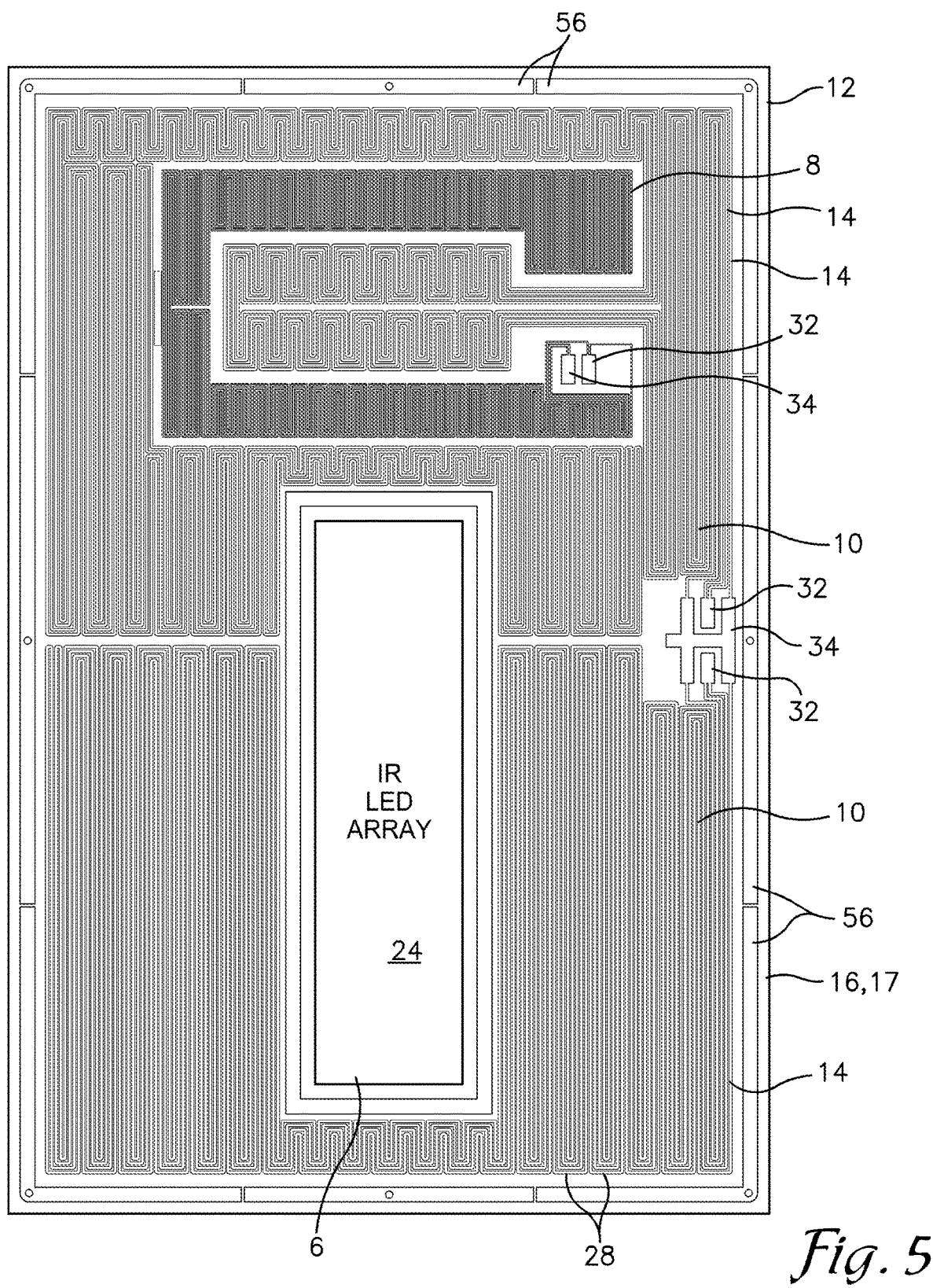
FIG. 5 is an elevational view of a substrate of an infrared panel diagrammatically illustrating radiant regions formed on the surface of the substrate to radiate infrared energy in selected infrared wavelength ranges in accordance with an exemplary embodiment.

FIG. 5 illustrates an embodiment of one of the substrates 16 or 17 having conductors 14 formed thereon. The substrates 16 and 17 preferably have patterns thereon which are substantially identical and which are positioned in close alignment in the panel 1. The conductors 14 of the substrates 16 and 17 are activated by the power supply 37 in opposite electrical polarities so that current flows in corresponding segments of the conductors 14 are in opposite directions whereby further cancellations of components of magnetic fields occur between corresponding conductors 14 of the substrates 16 and 17.

Figure 6:
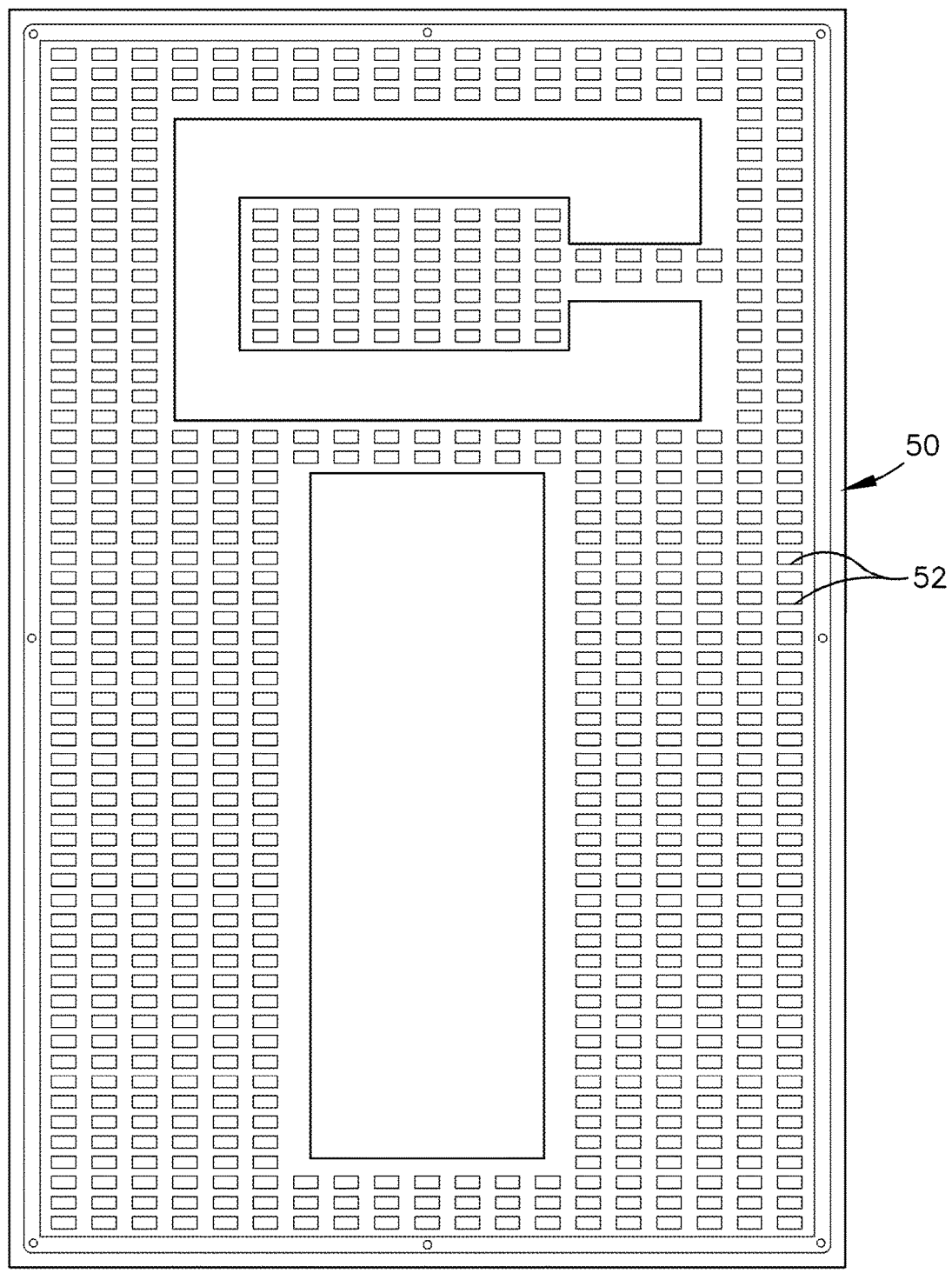
FIG. 6 is an elevational view of an exemplary conductive shield layer to suppress extremely low frequency electromagnetic fields which may be generated by currents flowing in resistive conductor traces of an infrared radiant panel depicted in accordance with an exemplary embodiment.
Figure 7:
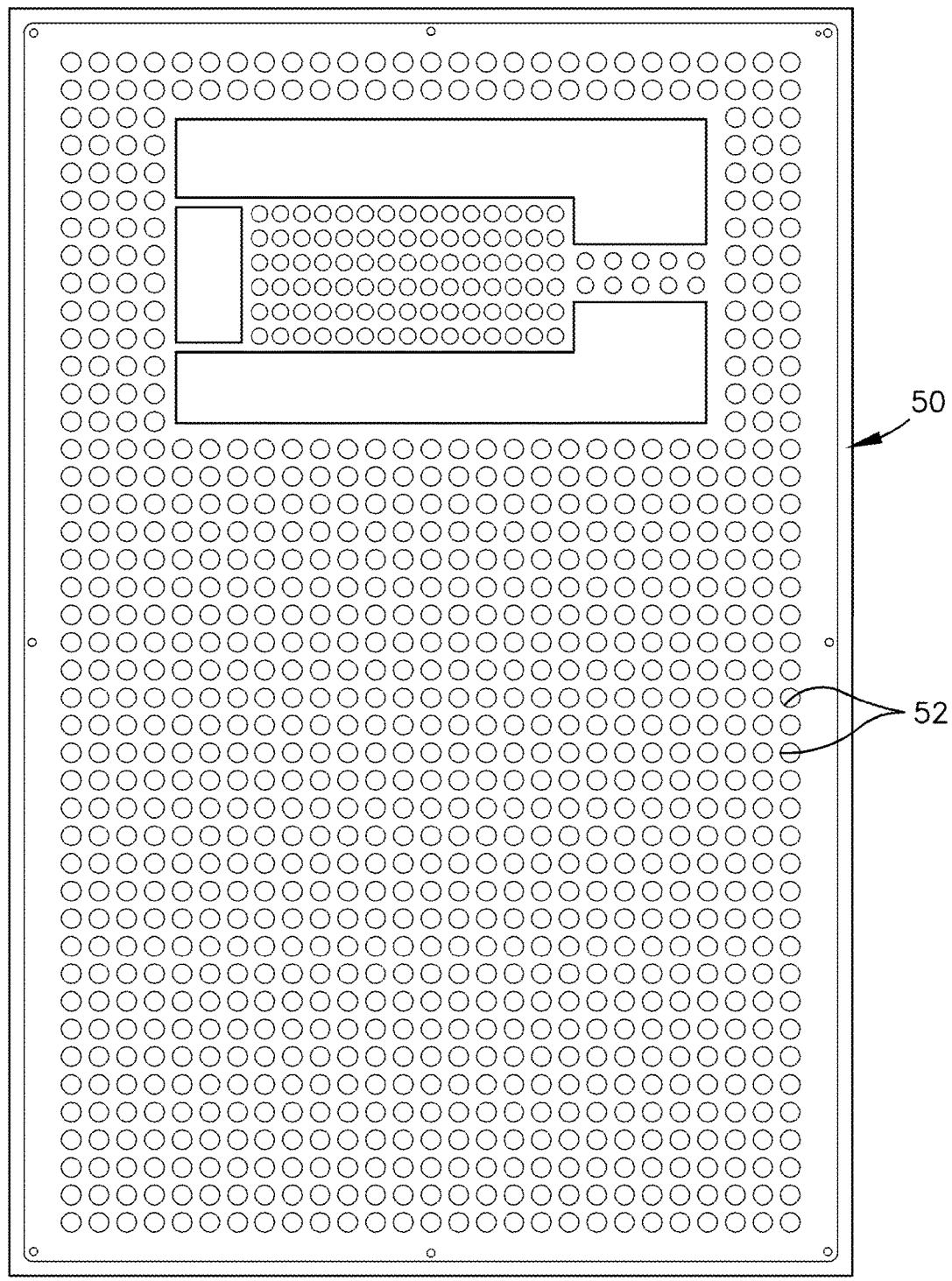
FIG. 7 is a view similar to FIG. 6 and illustrates an alternative conductive shield layer having patterns of rounded openings formed therethrough.

FIGS. 6 and 7 illustrate embodiments of an electromagnetic field (EMF) shield layer or shield 50 (also FIG. 3). The shield 50 may be a substrate formed of a polyimide polymer, polyvinyl chloride, or the like which has a conductive cladding thereon or laminated therein or therewith. The conductive nature of the shield 50 provides a barrier to electromagnetic field components generated by current in the conductors 14 which is not otherwise cancelled by the patterns 28 of the conductors. The illustrated shield 50 is configured particularly to overlay the far IR region 10 of the panel 1. It is foreseen that additional portions (not shown) of the shield 50 could be provided to overlay the near IR region 6 and the mid IR region 8 of the panel 1. The shield 50 may have a number of small openings 52 which enable efficient emission of infrared energy from the panel 1 without diminishing the ability of the shield 50 to act as an effective barrier to electromagnetic fields. The illustrated openings 52 in FIG. 6 are rectangular in shape. The openings 52 illustrated in FIG. 7 are rounded or circular in shape. It is also foreseen that the shield 50 could be formed with openings 52 have different sizes and shapes from those illustrated in FIGS. 6 and 7.

The substrates 12 may be joined in mutually overlapping relation to form the composite infrared radiant panel 1. The illustrated panel 1 is formed by fusing the substrates 12 together in a high temperature press. It is foreseen that the substrates 12 could alternatively be joined by adhesives, by fasteners, or by clamping them together by appropriately configured portions of the mounting frame 2. The panel 1 is supported in use by a frame or framework 2. In order to securely attach components of the frame 2 to the panel 1, the substrates 12 may be provided with strengthening or stiffening strips 56 (FIG. 5) along edges of the substrates. The strips 56 may be formed by strips of metallic cladding on the substrates 16 and 17 during the etching process to form the conductors 14. Alternatively, the strengthening strips 56 could be provided on other substrates 12 or all the substrates. The support frame 2 provides a means for mounting the infrared panel structure 3 on a wall or wall framing at a place of intended use.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A low EMF radiant infrared panel comprising:
   (a) at least one nonconductive substrate;
   (b) a first infrared region of the infrared panel formed in a first region of the at least one nonconductive substrate to radiate infrared energy in a first range of wavelengths and a second infrared region of the infrared panel formed in a second region of the at least one nonconductive substrate to radiate infrared energy in a second range of wavelengths, each of the first and second infrared regions including:
      (1) a first conductor formed on a first substrate surface of the at least one nonconductive substrate in a selected pattern;
      (2) a second conductor formed on a second substrate surface of the at least one nonconductive substrate in the selected pattern, the second conductor being positioned in close adjacent relation to the first conductor and being aligned therewith;
      (3) the first and second conductors receiving a level of current required to generate heat to cause infrared radiation in a range of wavelengths associated with the respective infrared region; and (4) the first and second conductors being electrically activated in opposite polarities to cause cancellation of first components of electromagnetic fields resulting from currents flowing in the first and second conductors;

(c) a conductive electromagnetic shield layer positioned in covering relation to the first and second infrared regions to suppress second electromagnetic field components resulting from currents flowing through the first and second conductors; and (d) each of the first and second conductors being a bifilar conductor which extends on its respective substrate surface in a pattern in which a first segment of each of the respective first and second conductors is positioned in closely adjacent, parallel relation with a second segment of the respective first and second conductors along the respective first and second conductors such that current flows in opposite directions in the first and second segments to thereby cause cancellation of components of electromagnetic fields generated by currents flowing in the segments.

2. A panel as set forth in claim 1, wherein the at least one nonconductive substrate comprises:

(a) a plurality of nonconductive substrates including a first and second nonconductive substrate;

(b) the first conductor of each of the first and second infrared regions being formed in the selected pattern on a surface of the first nonconductive substrate;

(c) the second conductor of each of the first and second infrared regions being formed in the selected pattern on a surface of the second nonconductive substrate; and (d) the first and second nonconductive substrates being positioned in adjacent overlying relation whereby the first and second conductors are positioned in close adjacent relation to cause cancellation of components of electromagnetic fields resulting from currents flowing in the first and second conductors.

3. A panel as set forth in claim 1, further comprising:

(a) a third infrared region formed on the panel by a plurality of infrared emitting diodes capable of radiating infrared energy in a third range of infrared wavelengths.

4. A panel as set forth in claim 1, further comprising:

(a) a direct current power supply coupled to the first and second conductors which causes the levels of current to flow therein to cause infrared radiation in the ranges of wavelengths associated with the respective first and second infrared regions.

5. A panel as set forth in claim 1 in combination with:

(a) a support frame having the panel structurally engaged therewith.

6. A panel as set forth in claim 1, wherein the at least one nonconductive substrate comprises:

(a) a plurality of nonconductive substrates, at least one of the plurality of nonconductive substrates having the conductors formed thereon; and (b) each of the plurality of nonconductive substrates being joined in mutually overlaying relation.

7. A panel as set forth in claim 1, further comprising:

(a) a thermostat thermally engaged with at least one of the first and second infrared regions; and (b) the thermostat being electrically coupled with the conductors associated with the respective first and second infrared region and controlling current flow therein to maintain a selected range of temperatures within the infrared region to thereby maintain the range of infrared wavelengths radiated by the respective first and second infrared region.

8. A panel as set forth in claim 1, further comprising:

(a) a thermal emissive material formed onto a surface of a substrate of the panel to enhance infrared radiation from the panel.

9. A panel as set forth in claim 1 wherein:

(a) a material is formed on a surface of the substrate to facilitate attachment of the substrate to a support frame.

10. A low EMF radiant infrared panel comprising:

(a) a plurality of nonconductive substrates, each substrate having opposite substrate surfaces;

(b) a first infrared region and a second infrared region formed on a surface of a first nonconductive substrate to radiate infrared energy respectively in a first range and a second range of wavelengths and on a surface of a second nonconductive substrate to radiate infrared energy in the first and second ranges of wavelengths, each of the infrared regions including:

(1) a first conductor formed on a surface of a first nonconductive substrate in a selected pattern; and (2) a second conductor formed on a surface of a second nonconductive substrate in the selected pattern;

(c) the substrates being joined in mutually overlaying relation to position the first conductor in closely adjacent aligned relation to the second conductor;

(d) the first and second conductors receiving levels of current required to generate heat to cause infrared radiation in a range of wavelengths associated with the respective infrared region;

(e) the first and second conductors being electrically activated in opposite polarities to cause cancellation of components of electromagnetic fields resulting from currents flowing in the conductors;

(f) a conductive electromagnetic shield layer positioned in covering relation to the first and second infrared regions to suppress additional electromagnetic field components resulting from currents flowing through conductors thereof; and (g) each of the first and second conductors being a bifilar conductor which extends on its respective substrate surface in a pattern in which a first segment of each first and second conductor is positioned in closely adjacent, parallel relation with a second segment of the respective first and second conductors along the respective first and second conductors such that current flows in opposite directions in the first and second segments to thereby cause cancellation of components of electromagnetic fields generated by currents flowing in the segments.

11. A panel as set forth in claim 10, further comprising:

(a) a third infrared region formed on the infrared panel by a plurality of infrared emitting diodes capable of radiating infrared energy in a third range of infrared wavelengths.

12. A panel as set forth in claim 10, further comprising:

(a) a direct current power supply coupled to the first and second conductors which causes the levels of current to flow therein to cause infrared radiation in the ranges of wavelengths associated with the respective infrared regions.

13. A panel as set forth in claim 10 in combination with:

(a) a support frame having the panel structurally engaged therewith.

14. A panel as set forth in claim 10, further comprising:
(a) a thermostat thermally engaged with at least one of the infrared regions; and
(b) the thermostat being electrically coupled with the conductors associated with the infrared region and controlling current flow therein to maintain a selected range of temperatures within the infrared region to thereby maintain the range of infrared wavelengths radiated by the infrared region.

15. A panel as set forth in claim 10, further comprising:
(a) a thermal emissive material formed onto a surface of a substrate of the panel to enhance infrared radiation from the panel.

16. A panel as set forth in claim 10 wherein:
(a) a material is formed on a surface of the substrate to facilitate attachment of the substrate to a support frame.

17. A panel as set forth in claim 1 wherein:
(a) the first conductor includes a first pair of bifilar conductors formed on the first surface;
(b) the second conductor includes a second pair of bifilar conductors formed on the second surface; and
(c) each of the pairs of bifilar conductors extend on their respective surface in a pattern in which segments of the first pair are positioned in closely adjacent, parallel relation with corresponding segments of the second pair.

18. A panel as set forth in claim 10 wherein:
(a) the first conductor includes a first pair of bifilar conductors formed on the first surface;
(b) the second conductor includes a second pair of bifilar conductors formed on the second surface; and
(c) each of the pairs of bifilar conductors extend on their respective surface in a pattern in which segments of the first pair are positioned in closely adjacent, parallel relation with corresponding segments of the second pair.

* * * * *